(12) United States Patent
Searle (10) Patent No.: US 6,495,609 B1
(45) Date of Patent: Dec. 17, 2002

(54) CARBON DIOXIDE RECOVERY IN AN ETHYLENE TO ETHYLENE OXIDE PRODUCTION PROCESS

(75) Inventor: Ronald G. Searle, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 42 days.

(21) Appl. No.: 09/705,846

(22) Filed: Nov. 3, 2000

(51) Int. Cl.⁷ .......................... C07C 27/00; C07C 1/00; C07D 317/00
(52) U.S. Cl. ................ 518/700; 518/703; 518/704; 585/639; 585/640; 549/534
(58) Field of Search ................ 518/700, 703, 518/704; 585/639, 640; 549/534

(56) References Cited

U.S. PATENT DOCUMENTS

| | | | |
|---|---|---|---|
| 2,936,303 A | 5/1960 | Goins | 260/93.7 |
| 3,258,455 A | 6/1966 | Natta et al. | 260/93.7 |
| 3,305,538 A | 2/1967 | Natta et al. | 260/93.7 |
| 3,364,190 A | 1/1968 | Emrick | 260/93.7 |
| 3,585,217 A | 6/1971 | Eckart | 260/348.5 |
| 3,635,803 A | 1/1972 | Binns et al. | 204/80 |
| 3,645,992 A | 2/1972 | Elston | 260/80.78 |
| 3,888,896 A | 6/1975 | Espino et al. | 260/449.5 |
| 3,957,448 A | 5/1976 | Sheuropeard et al. | 23/288 |
| 3,965,083 A | 6/1976 | Jezl et al | 526/65 |
| 3,971,768 A | 7/1976 | Peters et al. | 526/68 |
| 4,008,290 A | 2/1977 | Ward | 260/672 |
| 4,031,123 A | 6/1977 | Espino et al. | 260/449.5 |
| 4,041,095 A | 8/1977 | Kuo | 260/676 |
| 4,046,822 A | 9/1977 | Severino | 260/659 |
| 4,068,136 A | 1/1978 | Minami | 307/353 |
| 4,076,698 A | 2/1978 | Anderson et al. | 526/348.6 |
| 4,101,289 A | 7/1978 | Jezl et al. | 23/288 |
| 4,172,099 A | 10/1979 | Severino | 260/660 |
| 4,187,278 A | 2/1980 | Clifford | 422/132 |

(List continued on next page.)

FOREIGN PATENT DOCUMENTS

| | | |
|---|---|---|
| CA | 1157053 | 2/1981 |
| EP | 0 012 147 | 3/1979 |
| EP | 0 533 452 | 9/1992 |
| EP | 0 560 312 | 3/1993 |
| EP | 0 574 821 | 6/1993 |
| EP | 0 612 753 | 6/1999 |
| EP | 0 933 345 | 8/1999 |
| GB | 2039905 | 1/1979 |
| WO | WO 92/12184 | 7/1992 |
| WO | WO 93/24533 | 12/1993 |
| WO | WO 98/29464 | 7/1998 |

OTHER PUBLICATIONS

"MTO—has its time come?" Nitrogen & Methanol, No. 246, Jul.–Aug. 2000.
"New route to low–density polyethylene," Chemical Engineering, Dec. 3, 1979, pp. 80–85.
Barger et al., "Converting Natural Gas to Ethylene and Propylene by the UOP/Hydro MTO Process," 12$^{th}$ International Zeolite Conference 1999 Materials Research Society p. 567–573.
Blackwell et al. *Solid–State MNR of Silicoaluminophosphate Molecular Sieves and Aluminophosphate Materials*, J. Phys. Chem., vol. 92, pp. 3965–3970 (1988).
Chang, "Methanol Conversion to Light Olefins," Catal. Rev.–Sci. Eng., 26(3&4), 323–345 (1984).
Karol, Fredrick J., "The Polyethylene Revolution," Chemtech, Apr. 1983, pp. 222–228.
Kirk–Othmer Encyclopedia of Chemical Technology, 4th edition, vol. 9, John Wiley & Sons, pp. 894–899 (1996).

*Primary Examiner*—J. Parsa
(74) *Attorney, Agent, or Firm*—Paul T. Lavdig (57) ABSTRACT

Disclosed is a method for recovering carbon dioxide from an ethylene oxide production process and using the recovered carbon dioxide as a carbon source for methanol synthesis. More specifically, carbon dioxide recovered from an ethylene oxide production process is used to produce a syngas stream. The syngas stream is then used to produce methanol.

9 Claims, 1 Drawing Sheet

U.S. PATENT DOCUMENTS

| | | | | |
|---|---|---|---|---|
| 4,243,691 | A | 1/1981 | Mohlenkamp, Jr. et al. | 426/649 |
| 4,244,892 | A | 1/1981 | Guseinov et al. | 570/223 |
| 4,263,212 | A | 4/1981 | Hong et al. | 260/347.5 |
| 4,287,091 | A | 9/1981 | Selman | 252/429 |
| 4,302,565 | A | 11/1981 | Goeke et al. | 526/88 |
| 4,310,440 | A | 1/1982 | Wilson et al. | 252/435 |
| 4,318,800 | A | 3/1982 | Woebcke et al. | 208/127 |
| 4,340,769 | A | 7/1982 | Brandes et al. | 568/899 |
| 4,343,957 | A | 8/1982 | Sartorio et al. | 585/449 |
| 4,404,095 | A | 9/1983 | Haddad et al. | 208/161 |
| 4,419,221 | A | 12/1983 | Castagnos, Jr. et al. | 208/113 |
| 4,426,449 | A | 1/1984 | Geigert et al. | 435/155 |
| 4,433,188 | A | 2/1984 | Hoelderich et al. | 585/640 |
| 4,440,871 | A | 4/1984 | Lok et al. | 502/214 |
| 4,463,207 | A | 7/1984 | Johnson | 585/462 |
| 4,471,147 | A | 9/1984 | Owen et al. | 585/519 |
| 4,474,647 | A | 10/1984 | Asselineau et al. | 203/49 |
| 4,482,687 | A | 11/1984 | Noshay et al. | 526/125 |
| 4,499,327 | A | 2/1985 | Kaiser | 585/640 |
| 4,504,691 | A | 3/1985 | Hsia et al. | 585/519 |
| 4,508,842 | A | 4/1985 | Beran et al. | 502/112 |
| 4,521,631 | A | 6/1985 | Nishimura et al. | 564/478 |
| 4,524,229 | A | 6/1985 | Johnson | 585/463 |
| 4,554,392 | A | 11/1985 | Leuck et al. | 570/254 |
| 4,558,167 | A | 12/1985 | Riegel et al. | 570/238 |
| 4,567,029 | A | 1/1986 | Wilson et al. | 423/306 |
| 4,623,704 | A | 11/1986 | Dembicki et al. | 526/68 |
| 4,629,484 | A | 12/1986 | Kister | 62/29 |
| 4,659,685 | A | 4/1987 | Coleman, III et al. | 502/113 |
| 4,677,242 | A | 6/1987 | Kaiser | 585/638 |
| 4,677,243 | A | 6/1987 | Kaiser | 585/638 |
| 4,710,482 | A | 12/1987 | Job | 502/127 |
| 4,721,824 | A | 1/1988 | McWilliams et al. | 585/448 |
| 4,749,817 | A | 6/1988 | George et al. | 570/204 |
| 4,752,651 | A | 6/1988 | Kaiser | 585/640 |
| 4,861,743 | A | 8/1989 | Flank et al. | 502/214 |
| 4,861,939 | A | 8/1989 | Debras et al. | 585/820 |
| 4,956,426 | A | 9/1990 | Ardell et al. | 526/60 |
| 4,992,608 | A | 2/1991 | Cavani et al. | 585/467 |
| 5,019,143 | A | 5/1991 | Mehrta | 62/17 |
| 5,055,627 | A | 10/1991 | Smith, Jr. et al. | 585/467 |
| 5,068,475 | A | 11/1991 | Schmidhammer et al. | 570/262 |
| 5,096,684 | A | 3/1992 | Guth et al. | 423/306 |
| 5,102,841 | A | 4/1992 | Cann et al. | 502/112 |
| 5,102,848 | A | 4/1992 | Soo et al. | 502/218 |
| 5,126,308 | A | 6/1992 | Barger et al. | 502/214 |
| 5,144,090 | A | 9/1992 | Honda et al. | 568/476 |
| 5,183,936 | A | 2/1993 | Etzkorn et al. | 562/532 |
| 5,198,578 | A | 3/1993 | Etzkorn et al. | 562/532 |
| 5,235,088 | A | 8/1993 | Paparizos et al. | 558/324 |
| 5,238,892 | A | 8/1993 | Chang | 502/111 |
| 5,240,894 | A | 8/1993 | Burkhardt et al. | 502/108 |
| 5,243,115 | A | 9/1993 | Smith, Jr. et al. | 585/446 |
| 5,243,116 | A | 9/1993 | Lee et al. | 585/467 |
| 5,258,543 | A | 11/1993 | Suresh et al. | 558/325 |
| 5,262,575 | A | 11/1993 | Dianis | 570/235 |
| 5,262,576 | A | 11/1993 | Smith, Jr. | 585/447 |
| 5,274,138 | A | 12/1993 | Keating et al. | 549/529 |
| 5,280,074 | A | 1/1994 | Schreck et al. | 525/240 |
| 5,288,473 | A | 2/1994 | Shaw et al. | 423/237 |
| 5,300,707 | A | 4/1994 | Caillod et al. | 568/480 |
| 5,326,465 | A | 7/1994 | Yongqing et al. | 208/120 |
| 5,326,929 | A | 7/1994 | Mehra et al. | 585/809 |
| 5,349,072 | A | 9/1994 | Preston et al. | 549/529 |
| 5,364,915 | A | 11/1994 | Benham et al. | 526/105 |
| 5,432,243 | A | 7/1995 | Bodart | 526/68 |
| 5,504,166 | A | 4/1996 | Buchelli et al. | 526/60 |
| 5,523,502 | A | 6/1996 | Rubin et al. | 585/324 |
| 5,609,734 | A | 3/1997 | Streicher et al. | 203/39 |
| 5,681,908 | A | 10/1997 | Mehra et al. | 526/68 |
| 5,684,097 | A | 11/1997 | Palmroos et al. | 526/64 |
| 5,689,032 | A | 11/1997 | Krause et al. | 585/802 |
| 5,714,662 | A | 2/1998 | Vora et al. | 585/640 |
| 5,741,350 | A | 4/1998 | Rowles et al. | 95/42 |
| 5,744,680 | A | 4/1998 | Mulvaney, III et al. | 585/640 |
| 5,811,621 | A | 9/1998 | Van Dijk | 585/639 |
| 5,817,906 | A | 10/1998 | Marker et al. | 585/640 |
| 5,892,079 | A | 4/1999 | Wilson, Jr. | 556/11 |
| 5,907,076 | A | 5/1999 | Ou et al. | 585/800 |
| 5,914,433 | A | 6/1999 | Marker | 585/313 |
| 5,960,643 | A | 10/1999 | Kuechler et al. | 62/620 |
| 5,981,818 | A | 11/1999 | Purvis et al. | 585/519 |
| 5,990,369 | A | 11/1999 | Barger et al. | 585/640 |
| 6,173,584 | B1 | 1/2000 | Agrawal | 62/620 |
| 6,049,017 | A | 4/2000 | Vora et al. | 585/324 |
| 6,066,701 | A | 5/2000 | Koveal et al. | 526/64 |
| 6,069,288 | A | 5/2000 | Ou et al. | 585/800 |
| 6,121,503 | A | 9/2000 | Janssen et al. | 585/640 |
| 6,121,504 | A | 9/2000 | Kuechler et al. | 585/640 |

Figure

CARBON DIOXIDE RECOVERY IN AN ETHYLENE TO ETHYLENE OXIDE PRODUCTION PROCESS

FIELD OF INVENTION

This invention relates to recovering carbon dioxide from an ethylene oxide production process. In particular this invention relates to recovering carbon dioxide from an ethylene oxide production process and using the recovered carbon dioxide to produce methanol.

BACKGROUND OF THE INVENTION

Ethylene oxide is a major chemical raw material. Presently, about 9.6 million tons of ethylene oxide are produced world wide each year. The major use of ethylene oxide is for the manufacture of derivatives such as ethylene glycol, surfactants, and ethanolamines.

In the production of ethylene oxide 20–25% of the ethylene feed is oxidized into carbon dioxide and water instead of ethylene oxide. The loss of large quantities of ethylene and the environmental concerns in purging carbon dioxide into the environment has lead to attempts at minimizing the amount of carbon dioxide produced during the ethylene oxide production process.

Most of these efforts have concentrated on the selection of inhibitors and catalysts to increase ethylene oxide selectivity. For example, U.S. Pat. No. 5,102,848 to Soo et al. discloses the addition of fluoride anion to a catalyst reduces ethylene oxide combustion to carbon dioxide. U.S. Pat. No. 3,585,217 to Titzenthaler discloses that alkali metal chlorides can be used to counteract the formation of carbon dioxide during ethylene oxide production.

Instead of limiting the production of carbon dioxide during the ethylene oxide production process, the present invention provides for recovering the carbon dioxide. The recovered carbon dioxide is then used to produce methanol.

SUMMARY OF THE INVENTION

This invention provides a method of using carbon dioxide produced in an ethylene oxide reaction unit to produce methanol. Carbon dioxide produced during ethylene oxide production is used to produce syngas which is used to produce methanol.

In one embodiment, the invention provides a method of making methanol. The method comprises obtaining a carbon dioxide stream from an ethylene oxide production process, producing a syngas stream incorporating the carbon dioxide stream, and producing methanol from the syngas stream.

Preferably, the syngas stream produced has an SN from about 1.4 to about 2.4. Preferably, the syngas is produced using a steam reformer or a partial oxidation reformer. Preferably, the methanol produced is used as a feed to an olefin synthesis reactor. Preferably, the olefin synthesis reactor contains a molecular sieve catalyst selected from SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metallic containing forms thereof, or mixtures thereof. Preferably, the ethylene oxide production process comprises the catalytic oxidation of ethylene in the presence of a supported silver-based catalyst.

In another embodiment, the invention provides another method of making methanol. The method comprises introducing an ethylene stream into an ethylene oxide reaction unit and forming an ethylene oxide product within the ethylene oxide reaction unit. An ethylene oxide product stream and a carbon dioxide-containing vent stream are removed from ethylene oxide reaction unit. The carbon dioxide vent stream is used to produce a syngas stream. The syngas stream is used to produce methanol.

This invention will be better understood in combination with the following detailed description, and appended drawing and claims.

DETAILED DESCRIPTION OF THE INVENTION

Figure 1:
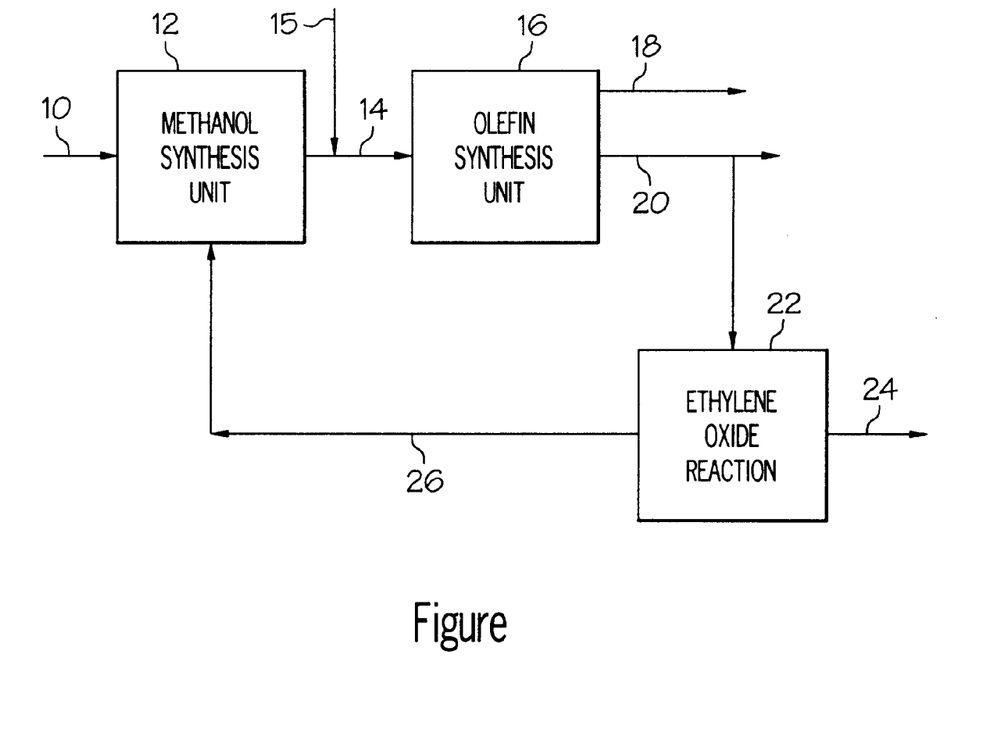
The FIGURE shows a flow diagram of the process of the invention.

This invention provides a method of using carbon dioxide produced in an ethylene oxide reaction unit to produce methanol. Catalytic oxidation of ethylene produces ethylene oxide as well as carbon dioxide and water. The carbon dioxide produced typically is of low value and is usually discarded. The invention combines an ethylene oxide reaction unit with a methanol generation unit. The methanol generation unit can utilize the carbon dioxide produced by the ethylene oxide production unit as a carbon source for methanol generation. The methanol produced by the methanol generation unit can then be fed to an olefin reaction unit to produce ethylene and other olefins. Ethylene produced can be used to produce ethylene derivatives such as polyethylene, or additional ethylene oxide.

An ethylene oxide reaction unit practiced as part of the invention preferably involves a direct oxidation process. A preferred direct oxidation process is the direct reaction of ethylene and oxygen over a silver containing catalyst. The direct oxidation occurs according to reaction (1).

Complete combustion of ethylene can also take place according to reaction (2).

The formation of carbon dioxide, which is usually considered an undesirable by-product in ethylene oxide production, is minimized by the introduction of vapor phase oxidation inhibitors. Preferred inhibitors include ethylene dichloride, vinyl chloride, and other halogenated compounds. The inhibitors suppress the combustion reaction by releasing chlorine atoms as they decompose. The chlorine atoms absorb onto the silver catalyst at sites where oxygen would absorb for the combustion reaction.

Some ethylene oxide is also lost by the oxidation of ethylene oxide to produce undesirable carbon dioxide and water according to reaction (3), during the production of ethylene oxide.

Both reactions (2) and (3) are exothermic. The selectivity of reaction (1) over reactions (2) and (3) is a function of operating conditions and the concentration of other gases.

Activity and selectivity are typically balanced in the design of a suitable catalyst. Typically, the balance of activity and selectivity limits the conversion of ethylene into ethylene oxide to between 10% and 20% of the ethylene in the reactor. This means that about 80%/o to 90% of the ethylene in the reactor is not converted into ethylene oxide in a single pass through the ethylene oxide reactor. To obtain higher yields, unreacted ethylene is separated out and then recycled back to the ethylene oxide reactor.

In addition to ethylene oxide, carbon dioxide, and water, formaldehyde and acetaldehyde may also be produced during the ethylene oxide production process. Generally, the formaldehyde and acetaldehyde produced amount to less than 0.2% of the ethylene oxide formed.

Conventional catalysts capable of converting ethylene into ethylene oxide can be used in the invention. A preferred catalyst is a silver based catalyst. The silver may be supported or unsupported. A more preferred catalyst, however, is a supported silver-based catalyst. Preferred supports include alundum, silicon carbide, aluminum oxide, glass wool, quartz, carborundum, and ion exchange zeolites. Particularly desirable supports are alundum and silicon carbide. The catalyst can be formed into spheres or rings, and preferably have pore diameters of 0.5 micrometers to 50 micrometers and a total surface area less than 2 $m^2/g$.

Alkali metal promoters can also be added to the catalyst, preferably cesium. The alkali metal promoters can be added to the catalyst by adding an alkali metal salt to the catalyst mixture during catalyst manufacturing.

The selectivity of preferred silver based catalysts ranges from about 75% to about 95%. As the catalyst ages, the selectivity of the catalyst goes down due to abrasion, deposition of carbon-containing compounds, and recrystallization of the silver in the catalyst. The typical life span of the catalyst is from two to five years.

Any conventional reactor can be used as part of the invention. A preferred process utilizes a gas phase reaction where ethylene and oxygen are reacted in a multitubular reactor. Typical reactor conditions include a pressure of about 10 atm to about 30 atm. and a temperature of 200° C. to 300° C. Typically, the tubes in the reactor are mild steel or stainless steel and are 6 meters to 12 meters long and 20 millimeters to 50 millimeters in diameter. The reactors are usually cooled using oil or boiling water.

The oxidation of ethylene to form ethylene oxide can use either air or high purity oxygen (typically >95 mol %) as an oxygen source. Although either air or high purity oxygen can be used as an oxygen source in the ethylene oxide production process, both processes produce a large amount of carbon dioxide and water. Generally, about 20% to about 25% of the ethylene used in the ethylene oxide production process is oxidized into carbon dioxide and water.

In air based ethylene oxide production processes, carbon dioxide purged from the process can contain a large amount of other gasses, particularly nitrogen. The carbon dioxide may need to be separated from these other gasses before further use of the carbon dioxide. In a preferred oxygen based process, the quantities of other gasses such as nitrogen are reduced allowing for a purer carbon dioxide purge stream emanating from the process.

In this invention, carbon dioxide produced during the ethylene oxide production process is provided to make methanol. This use of carbon dioxide can may make ethylene oxide production more economical. A catalyst that converts ethylene to ethylene oxide faster, a higher activity catalyst, can be used even if this catalyst has produces more carbon dioxide and water, a lower selectivity catalyst. A higher activity catalyst that has a lower selectivity could be used to produce ethylene oxide since excess carbon dioxide produced can be used in the present invention.

Methanol synthesis via syngas can utilize carbon dioxide as a carbon source to produce methanol. Syngas is defined as a gas comprising carbon monoxide, carbon dioxide, and hydrogen. Other gases present in syngas may include methane and small amounts of light paraffins, such as ethane and propane.

One way of characterizing the composition of a syngas stream used for methanol synthesis is to account for the $CO_2$ present in the syngas stream. The syngas number (SN) is defined as follows:

$$SN=(H_2-CO_2)/(CO+CO_2)$$

$H_2$, $CO_2$, and CO represents the molar percentage of hydrogen, carbon dioxide, and carbon monoxide respectfully.

A higher SN number represents a hydrogen rich syngas stream, and a lower SN number represents a carbon rich syngas stream. The syngas stream to a methanol reactor desirably has a SN of from about 1.4 to about 2.4, preferably of from about 1.8 to about 2.2, and most preferably from about 2.0 to about 2.1.

A desirable initial step in the production of methanol from syngas is to produce syngas from a methane-containing gas, such as natural gas or refinery off-gas. Syngas can be generated using steam reforming or partial oxidation reforming, which includes combined reforming and autothermal reforming processes.

Steam reforming is the catalytic reaction of methane with steam to produce $H_2$ and CO, reaction (4).

$$H_2O(g)+CH_4 \rightarrow 3H_2+CO \qquad (4)$$

$CO_2$ is also produced because the steam reacts with the CO according to what is known as the water-gas shift reaction (5) to produce $CO_2$ and $H_2$.

$$CO_2+H_2 \leftrightarrows CO+H_2O \qquad (5)$$

A steam reformer typically produces syngas with a SN of greater than about 2.8. This high SN number means that a steam reformer produces excess hydrogen, i.e., a hydrogen rich syngas stream. The excess hydrogen produced by a steam reformer can be utilized by the addition of carbon dioxide to the syngas stream emanating from a steam reformer. In this invention, the carbon dioxide produced from the ethylene oxide production process is used as a carbon dioxide source.

A conventional steam reformer can be used in the invention. In such a case, it is preferred to use a commercial nickel catalyst such as obtained from Katalco and designated as 23-1. The reactions take place inside tubular reactors, which are filled with catalyst. The tubular reactors are contained inside a combustion chamber. Steam reforming is highly endothermic. Thus, large amounts of heat must be supplied to the process. A portion of the natural gas can be used as fuel to provide the necessary heat for the reaction. The pressure inside the tubes is preferably 100 psia to 500 psia and the temperature at tube outlets is preferably about 700° C. to about 900° C. The residence time of the gas stream inside the interior of the catalytic beds can range from about four to six seconds. The flow of input gases through the reactor catalyst bed is preferably 200 lbs/hr/$ft^3$ to 400 lbs/hr/$f^3$ of catalyst. A preferred catalyst in this process is Ni supported on an aluminum, magnesium, or silicon oxide substrate.

Syngas can also be produced from methane by a catalytic oxidation process. An oxygen containing gas is fed into a reactor or reactor feed pipe where it mixes with methane. The oxygen reacts with the methane to form CO, $CO_2$ and $H_2$. A partial oxidation reactor ($PO_xR$), can be used. The ($PO_xR$) desirebly produces a syngas stream with a SN of about 1.4 to about 2.1.

A lower SN number, e.g. a syngas number less than about 2, means that less hydrogen is produced relative to the amount of carbon dioxide. Partial oxidation is the reaction of natural gas with controlled amounts of oxygen, reaction (6).

$$CH_4 + 1/2 O_2 \rightarrow CO + 2H_2 \quad (6)$$

However, in a commercial setting, this reaction is difficult to carry out as written. There will generally be some production of water and carbon dioxide, and a desirable SN for partial oxidation will be about 1.3 to about 1.7.

As with the steam reformer, relatively high temperatures and low pressures favor production of syngas. However, once the reactants have been preheated, the reaction is self-sustaining without the need of additional heat. The process temperatures are preferably from about 1250° C. to about 1500° C., and the pressures preferably range from about 450 psia to about 1800 psia. A preferred reactant ($O_2$:$CH_4$) mixture ratio of about 0.4 to about 0.8 (by vol/vol) is desired, and large amounts of $CO_2$ are produced.

An autothermal reformer, which combines partial oxidation and adiabatic steam reforming, can also be used in this invention. In this process, methane is nearly completely converted to CO in a combustion type reaction, reaction (7). In addition, uncombusted methane can be catalytically reacted with water to produce CO and $H_2$, reaction (8), as in a steam reformer. Equation 9 shows the theoretical syngas composition for an autothermal reformer, which is the combination of reactions (7) and (8).

$$CH_4 + \tfrac{1}{2} O_2 \rightarrow CO + 2H_2O \quad (7)$$

$$CH_4 + H_2O \; CO + 3H_2 \quad (8)$$

$$2CH_4 + \tfrac{1}{2} O_2 \rightarrow CO + 3H_2 + H_2O \quad (9)$$

Because the water gas shift reaction is also occurring, $CO_2$ is present in the output syngas stream. Some $CO_2$ is also produced in the combustion zone. The $CO_2$ is often recycled back to the reformer to optimize a select output syngas composition. An autothermal reformer preferably produces syngas with a SN from about 1.6 to about 2.1.

A preferred reaction system for an autothermal reformer includes a refractory lined reactor. Catalysts that can be used in the autothermal reformer are preferably similar to those used in a steam reformer. The reactor outlet temperature is preferably about 900° C. to about 1000° C., although the temperature within the combustion zone of the reactor can be considerably higher. The reactor pressure is preferably about 300 to about 1200 psia.

Another preferred embodiment of the invention includes combined reforming. This process combines an endothermic (heat is added) steam reformer with an exothermic (heat is released) oxidation reformer. In a preferred design configuration, about 35% to about 65% of the total natural gas sent to the combined reforming system is fed to the steam reformer to produce a reformed gas. The reformed gas is then blended with the remainder of the natural gas (i.e., about 35% to about 65%) and oxygen, and introduced to an autothermal reformer. The advantage of combining the steam reformer with the autothermal reformer is that a SN of about 1.9 to about 2.1 is obtained. Also, an autothermal reformer can operate at decreased oxygen consumption, thus lowering the costs of production.

$CO_2$ produced from the ethylene oxide production process can be added to either the syngas generator or to the produced syngas entering a methanol synthesis reactor. The addition of $CO_2$ can have at least two effects on methanol synthesis. One, the $CO_2$ can react with excess hydrogen to produce more CO according to the well known water-gas shift reaction (5). The water-gas shift reaction provides a route to more CO if the $CO_2$ is directed to the steam reformer and/or to a partial oxidation reformer. Two, the $CO_2$ in combination with excess hydrogen can be used as a carbon source to produce more methanol. This is particularly desirable when operated at a SN of about 2.0 to about 2.1.

The synthesis of methanol from syngas is based on the equilibrium reactions of syngas reactions (10) and (11).

$$CO + 2H_2 \leftrightharpoons CH_3OH \quad (10)$$

$$CO_2 + 3H_2 \leftrightharpoons CH_3OH + H_2O \quad (11)$$

The forward reactions (10) and (11) are exothermic. That is, they result in the formation of net heat. Also, the forward reactions (10) and (11) generate less volumes of MeOH (gas) than the volumes of feed (gas) used to form the methanol. Therefore, to maximize methanol yields, i.e., to force reactions (10) and (11) to the right, it is preferred to operate at low temperatures and high pressures in order to get high conversion to methanol product. To obtain higher conversions, unreacted syngas is desirably separated from the methanol product and recycled back to the reactor or directed to a second reactor to produce additional methanol.

Desirably, two types of methanol synthesis reactors can be used in the invention: a slurry type reactor or a fixed-bed reactor. The methanol synthesis reactor can be a conventional high pressure reactor operating at about 500 to about 2000 psi, or a low pressure methanol synthesis reactor operating at about 200 to about 700 psi.

In a preferred embodiment of the invention, a liquid phase methanol reactor can be used. The liquid phase methanol synthesis reactor can be any suitable reactor that is capable of converting a syngas feed stream to methanol. Such reactors are described in U.S. Pat. Nos. 3,888,896 and 4,031,123 and Canadian Pat. No. 1,157,053, the catalyst and process descriptions of each being expressly incorporated herein by reference.

The liquid phase methanol reactor includes an active methanol synthesis catalyst suspended in an inert hydrocarbon liquid, preferably a mineral oil. Synthesis gas is preferably bubbled through the catalyst-oil mixture where a portion of the $H_2$, CO and $CO_2$ in the synthesis gas is converted to methanol. The synthesis catalyst can be pellet-sized and fluidized by the inert liquid, or it can be a powdered catalyst contained in the liquid, forming a slurry.

A liquid phase methanol synthesis reactor operates at a pressure from about 400 to about 1200 psia. The reactor temperature is preferably from about 150° C. to about 400° C., with preferred temperatures from about 200° C. to about 300° C. Reactor space velocity, in units of feed per hour per kilogram of catalyst, is preferably from about 4000 to about 10,000 for the slurry mode reactor operation and from about 2000 to about 6000 for the fluidized mode. High single pass conversions are achievable in the liquid phase methanol reactor.

The catalyst used in the liquid phase methanol reactor can be conventional methanol-forming catalyst. Preferred methanol forming catalyst have active elements selected from the group consisting of copper, zinc, chromium, aluminium, tungsten, vanadium, magnesium, and the rare earth elements. Average catalyst particle sizes can range from 0.00002 to 0.25 inches. Higher aliphatic alcohols can also be produced along with the methanol. The higher aliphatic alcohols can be condensed and recovered with the methanol as a combined product, or separated and recovered as an additional product.

Another preferred embodiment of the invention includes a "low pressure" gas phase methanol synthesis reaction process. This process preferably uses Cu/ZnO or Cu/ZnO/$Al_2O_3$ as a catalyst and operates from about 200° C. to about 300° C. and from about 50 to about 110 atm. In this process, methanol synthesis is desirably carried out in the gas phase in a fixed bed reactor. The process provides low power requirements, good catalyst life, larger capacity single-train converter designs and improved reliability.

The methanol produced in this invention can be used as feed or co-feed in a methanol-to-olefin (MTO) conversion process. It may be desirable to first purify the methanol prior to its use in the MTO process. In a methanol purification unit most of the water, methanol, and reaction by-products, such as ethers, other alcohols, aldehydes, ketones, etc., can be removed in the condensate phase and fed to a multi column distillation train if desired.

Preferable co-feeds used in this invention comprise organic compounds that contain at least one oxygen atom, such as aliphatic alcohols, ethers, carbonyl compounds (aldehydes, ketones, carboxylic acids, carbonates, esters and the like). When the co-feed is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate co-feed compounds include, but are not limited to: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof Preferred oxygenate co-feed compounds are methanol, dimethyl ether, or a mixture thereof One or more inert diluents may be present in the feedstock to the conversion process, for example, in an amount of from 1 to 99 molar percent, based on the total number of moles of all feed and diluent components fed to the reaction zone (or catalyst). As defined herein, diluents are compositions which are essentially non-reactive across a molecular sieve catalyst, and primarily function to make the methanol in the feedstock less concentrated. Typical diluents include, but are not necessarily limited to helium, argon, nitrogen, carbon monoxide, carbon dioxide, water, essentially non-reactive paraffins (especially the alkanes such as methane, ethane, and propane), essentially non-reactive alkylenes, essentially non-reactive aromatic compounds, and mixtures thereof The preferred diluents are water and nitrogen. Water can be injected in either liquid or vapor form.

Hydrocarbons can also be included as part of the feedstock, i.e., as additional co-feed. As defined herein, hydrocarbons included with the methanol are hydrocarbon compositions which are converted to another chemical arrangement when contacted with molecular sieve catalyst. These hydrocarbons can include olefins, reactive paraffins, reactive alkylaromatics, reactive aromatics or mixtures thereof Preferred hydrocarbon co-feeds include, propylene, butylene, pentylene, $C_4^+$ hydrocarbon mixtures, $C_5^+$ hydrocarbon mixtures, and mixtures thereof More preferred as co-feeds are a $C_4^+$ hydrocarbon mixtures, with the most preferred being $C_4^+$ hydrocarbon mixtures which are obtained from separation and recycle of reactor product.

In the MTO process of this invention, coked catalyst produced in the reactor can be regenerated by contacting the coked catalyst with a regeneration medium to remove all or part of the coke deposits. This regeneration can occur periodically within the reactor by ceasing the flow of feed to the reactor, introducing a regeneration medium, ceasing flow of the regeneration medium, and then reintroducing the feed to the fully or partially regenerated catalyst. Regeneration may also occur periodically or continuously outside the reactor by removing a portion of the deactivated catalyst to a separate regenerator, regenerating the coked catalyst in the regenerator, and subsequently reintroducing the regenerated catalyst to the reactor. Regeneration can occur at times and conditions appropriate to maintain a desired level of coke on the entire catalyst within the reactor.

Catalyst that has been contacted with feed in a MTO reactor is defined herein as "feedstock exposed." Feedstock exposed catalyst will provide olefin conversion reaction products having substantially lower propane and coke content than a catalyst which is fresh and regenerated. A catalyst will typically provide lower amounts of propane as it is exposed to more feed, either through increasing time at a given feed rate or increasing feed rate over a given time.

Any standard MTO reactor system can be used, including fixed bed, fluid bed or moving bed systems. Preferred reactors are co-current riser reactors and short contact time, countercurrent free-fall reactors. Desirably, the MTO reactor is one in which an oxygenate feedstock can be contacted with a molecular sieve catalyst at a weight hourly space velocity (WHSV) of at least about 1 $hr^{-1}$, preferably in the range of from about 1 $hr^{-1}$ to about 1000 $hr^{-1}$, more preferably in the range of from about 20 $hr^{-1}$ to about 1000 $hr^{-1}$, and most preferably in the range of from about 20 $hr^{-1}$ to about 500 $hr^{-1}$. WHSV is defined herein as the weight of oxygenate, and hydrocarbon which may optionally be in the feed, per hour per weight of the molecular sieve content of the catalyst. Because the catalyst or the feedstock may contain other materials which act as inerts or diluents, the WHSV is calculated on the weight basis of the oxygenate feed, and any hydrocarbon which may be present, and the molecular sieve contained in the catalyst.

Preferably, the feed to the MTO reactor is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The MTO process can generally be carried out at a wide range of temperatures. An effective operating temperature range can be from about 200° C. to about 700° C., preferably from about 300° C. to about 600° C., more preferably from about 350° C. to about 550° C. At the lower end of the temperature range, the formation of the desired olefin products may become markedly slow. At the upper end of the temperature range, the process may not form an optimum amount of product.

The MTO process may be carried out in a variety of catalytic reactors. Reactor types include fixed bed reactors, fluid bed reactors, and concurrent riser reactors. Additionally, countercurrent free fall reactors may be used in the conversion process.

In a preferred embodiment of the continuous operation of the MTO process, only a portion of the catalyst is removed from the reactor and sent to the regenerator to remove the accumulated coke deposits that result during the catalytic reaction. In the regenerator, the catalyst is contacted with a regeneration medium containing oxygen or other oxidants. Examples of other oxidants include $O_3$, $SO_3$, $N_2O$, NO, $NO_2$, $N_2O_5$, and mixtures thereof It is preferred to supply $O_2$ in the form of air. The air can be diluted with nitrogen, $CO_2$, or flue gas, and steam may be added. Desirably, the $O_2$ concentration in the regenerator is reduced to a controlled level to minimize overheating or the creation of hot spots in the spent or deactivated catalyst. The deactivated catalyst also may be regenerated reductively with $H_2$, CO, mixtures thereof, or other suitable reducing agents. A combination of oxidative regeneration and reductive regeneration can also be employed.

In essence, the coke deposits are removed from the catalyst during the regeneration process, forming a regenerated catalyst. The regenerated catalyst is then returned to the reactor for further contact with feed. Typical regeneration temperatures are from 250° C. to 700° C., desirably from 350° C. to 700° C. Preferably, regeneration is carried out at a temperature of 450° C. to 700° C.

It is desirable to strip at least some of the volatile organic components which may be adsorbed onto the catalyst or located within its microporous structure prior to entering the regenerator. This can be accomplished by passing a stripping gas over the catalyst in a stripper or stripping chamber, which can be located within the reactor or in a separate vessel. The stripping gas can be any substantially inert medium that is commonly used. Examples of stripping gas are steam, nitrogen, helium, argon, methane, $CO_2$, CO, flue gas, and hydrogen.

In one embodiment, the reactor and regenerator in the MTO process are configured such that the feed contacts the regenerated catalyst before it is returned to the reactor. In an alternative embodiment, the reactor and regenerator are configured such that the feed contacts the regenerated catalyst after it is returned to the reactor. In yet another embodiment, the feed stream can be split such that feed contacts regenerated catalyst before it is returned to the reactor and after it has been returned to the reactor.

The catalyst that is used in the MTO process is preferably one that incorporates a silicoaluminophosphate (SAPO) molecular sieve. The molecular sieve comprises a three-dimensional microporous crystal framework structure of $[SiO_2]$, $[AlO_2]$ and $[PO_2]$ corner sharing tetrahedral units. The way Si is incorporated into the structure can be determined by $^{29}Si$ MAS NMR. See Blackwell and Patton, *J. Phys. Chem.*, 92, 3965 (1988). The desired SAPO molecular sieves will exhibit one or more peaks in the $^{29}Si$ MAS NMR, with a chemical shift $\alpha$ (Si) in the range of –88 to –96 ppm and with a combined peak area in that range of at least 20% of the total peak area of all peaks with a chemical shift $\beta$ (Si) in the range of –88 ppm to –115 ppm, when the $\beta$ (Si) chemical shifts refer to external tetramethylsilane (Tmethanol synthesis).

It is preferred that the silicoaluminophosphate molecular sieve used in this invention have a relatively low $Si/Al_2$ ratio. In general, the lower the $Si/Al_2$ ratio, the lower the $C_1$–$C_4$ saturates selectivity, particularly propane selectivity. A $Si/Al_2$ ratio of less than 0.65 is desirable, with a $Si/Al_2$ ratio of not greater than 0.40 being preferred, and a $Si/Al_2$ ratio of not greater than 0.32 being particularly preferred. A $Si/Al_2$ ratio of not greater than 0.20 is most preferred.

Silicoaluminophosphate molecular sieves are generally classified as being microporous materials having 8, 10, or 12 membered ring structures. These ring structures can have an average pore size ranging from about 3.5 angstroms to about 15 angstroms. Preferred are the small pore SAPO molecular sieves having an average pore size of less than about 5 angstroms, preferably an average pore size ranging from about 3.5 angstroms to about 5 angstroms, more preferably from about 3.5 angstroms to about 4.2 angstroms. These pore sizes are typical of molecular sieves having 8 membered rings.

In general, silicoaluminophosphate molecular sieves comprise a molecular framework of corner-sharing $[SiO_2]$, $[AlO_2]$, and $[PO_2]$ tetrahedral units. This type of framework is effective in converting various oxygenates into olefin products.

The $[PO_2]$ tetrahedral units within the framework structure of the molecular sieve of this invention can be provided by a variety of compositions. Examples of these phosphorus-containing compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The $[AlO_2]$ tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The $[SiO_2]$ tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Substituted SAPOs can also be used in this invention. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a $[MeO_2]$ tetrahedral unit. The $[MeO_2]$ tetrahedral unit carries a net electric charge depending on the valence state of the metal substituent. When the metal component has a valence state of +2, +3, +4, +5, or +6, the net electric charge is between –2 and +2. Incorporation of the metal component is typically accomplished adding the metal component during synthesis of the molecular sieve. However, post-synthesis ion exchange can also be used. In post synthesis exchange, the metal component will introduce cations into ion-exchange positions at an open surface of the molecular sieve, not into the framework itself.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-4.0, SAPO-41, SAPO-42, SAPO-44, SAPO-47, SAPO-56, the metal containing forms thereof, and mixtures thereof. Preferred are SAPO-17, SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

An aluminophosphate (ALPO) molecular sieve can also be included in the catalyst composition. Aluminophosphate molecular sieves are crystalline microporous oxides which can have an $AlPO_4$ framework. They can have additional elements within the framework, typically have uniform pore dimensions ranging from about 3 angstroms to about 10 angstroms, and are capable of making size selective separations of molecular species. More than two dozen structure types have been reported, including zeolite topological analogues. A more detailed description of the background and synthesis of aluminophosphates is found in U.S. Pat. No. 4,310,440, which is incorporated herein by reference in its entirety. Preferred ALPO structures are ALPO-5, ALPO-11, ALPO-18, ALPO-31, ALPO-34, ALPO-36, ALPO-37, and ALPO-46.

The silicoaluminophosphate molecular sieves are synthesized by hydrothermal crystallization methods generally known in the art. See, for example, U.S. Pat. Nos. 4,440,871; 4,861,743; 5,096,684; and 5,126,308, the methods of making of which are fully incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100° C. to 250° C., until a crystalline product is formed.

Formation of the crystalline product can take anywhere from around 2 hours to as much as 2 weeks. In some cases, stirring or seeding with crystalline material will facilitate the formation of the product.

Typically, the molecular sieve product is formed in solution. It can be recovered by standard means, such as by centrifugation or filtration. The product can also be washed, recovered by the same means, and dried.

As a result of the crystallization process, the recovered sieve contains within its pores at least a portion of the template used in making the initial reaction mixture. The crystalline structure essentially wraps around the template, and the template must be removed so that the molecular sieve can exhibit catalytic activity. Once the template is removed, the crystalline structure that remains has what is typically called an intracrystalline pore system.

In many cases, depending upon the nature of the final product formed, the template may be too large to be eluted from the intracrystalline pore system. In such a case, the template can be removed by a heat treatment process. For example, the template can be calcined, or essentially combusted, in the presence of an oxygen-containing gas, by contacting the template-containing sieve in the presence of the oxygen-containing gas and heating at temperatures from 200° C. to 900° C. In some cases, it may be desirable to heat in an environment having a low oxygen concentration. In these cases, however, the result will typically be a breakdown of the template into a smaller component, rather than by the combustion process. This type of process can be used for partial or complete removal of the template from the intracrystalline pore system. In other cases, with smaller templates, complete or partial removal from the sieve can be accomplished by conventional desorption processes such as those used in making standard zeolites.

The reaction mixture can contain one or more templates. Templates are structure directing or affecting agents, and typically contain nitrogen, phosphorus, oxygen, carbon, hydrogen or a combination thereof, and can also contain at least one alkyl or aryl group, with 1 to 8 carbons being present in the alkyl or aryl group. Mixtures of two or more templates can produce mixtures of different sieves or predominantly one sieve where one template is more strongly directing than another.

Representative templates include tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof Preferred templates are triethylamine, cyclohexylamine, piperidine, pyridine, isopropylamine, tetraethyl ammonium salts, dipropylamine, and mixtures thereof. The tetraethylammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Preferred tetraethyl ammonium salts are tetraethyl ammonium hydroxide and tetraethyl ammonium phosphate.

The SAPO molecular sieve structure can be effectively controlled using combinations of templates. For example, in a particularly preferred embodiment, the SAPO molecular sieve is manufactured using a template combination of TEAOH and dipropylamine. This combination results in a particularly desirable SAPO structure for the conversion of oxygenates, particularly methanol and dimethyl ether, to light olefins such as ethylene and propylene.

The silicoaluminophosphate molecular sieve is typically admixed (i.e., blended) with other materials. When blended, the resulting composition is typically referred to as a SAPO catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof. These components are also effective in reducing, inter alia, overall catalyst cost, acting as a thermal sink to assist in heat shielding the catalyst during regeneration, densifying the catalyst and increasing catalyst strength. It is particularly desirable that the inert materials that are used in the catalyst to act as a thermal sink have a heat capacity of from about 0.05 cal/g-° C. to about 1 cal/g-° C., more preferably from about 0.1 cal/g-° C. to about 0.8 cal/g-° C., most preferably from about 0.1 cal/g-° C. to about 0.5 cal/g-° C.

Additional molecular sieve materials can be included as a part of the SAPO catalyst composition or they can be used as separate molecular sieve catalysts in admixture with the SAPO catalyst if desired. Structural types of small pore molecular sieves that are suitable for use in this invention include AEI, AFT, APC, ATN, ATT, ATV, AWW, BIK, CAS, CHA, CfH, DAC, DDR, EDI, ERI, GOO, KFI, LEV, LOV, LTA, MON, PAU, PHI, RHO, ROG, THO, and substituted forms thereof Structural types of medium pore molecular sieves that are suitable for use in this invention include MFI, MEL, MTW, EUO, MTT, HEU, FER, AFO, AEL, TON, and substituted forms thereof. Preferred molecular sieves which can be combined with a silicoaluminophosphate catalyst include ZSM-5, ZSM-34, erionite, and chabazite.

The MTO process of the invention can be polymerized to form polyolefins, particularly polyethylene and polypropylene. Catalytic processes are preferred. Particularly preferred are metallocene, Ziegler/Natta and acid catalytic systems. See, for example, U.S. Pat. Nos. 3,258,455; 3,305, 538; 3,364,190; 5,892,079; 4,659,685; 4,076,698; 3,645, 992; 4,302,565; and 4,243,691, the catalyst and process descriptions of each being expressly incorporated herein by reference for the purposes of United States patent practice.

In general, these methods involve contacting the olefin product with a polyolefin-forming catalyst at a pressure and temperature effective to form the polyolefin product.

A preferred polyolefin-forming catalyst is a metallocene catalyst. The preferred temperature range of operation is from about 50° C. to about 240° C., and the reaction can be carried out at low, medium or high pressure, being anywhere within the range of about 1 bar to about 200 bars. For processes carried out in solution, an inert diluent can be used, and the preferred operating pressure range is from about 10 bars to about 150 bars, with a preferred temperature range of about 120° C. to about 230° C. For gas phase processes, it is preferred that the temperature generally be within a range of about 60° C. to about 160° C., and that the operating pressure be from about 5 bars to about 50 bars.

A preferred embodiment of the present invention is shown in the FIGURE. In the FIGURE, a natural gas stream 10, along with a carbon dioxide containing stream 26, is fed into a methanol synthesis unit 12 which preferably includes a syngas generator and a methanol reactor. The methanol synthesis unit 12 first converts the natural gas into syngas. The syngas can be produced using methane reforming, partial oxidation reforming, combined reforming, and/or autothermal reforming processes. The syngas produced from the natural gas stream is combined with the carbon dioxide from stream 26 to produce a more carbon rich syngas stream. The carbon rich syngas stream is fed into a methanol reactor in the methanol synthesis unit 12. The methanol reactor produces a methanol stream 14, from the carbon rich syngas. Methanol stream 14, is fed into an olefin synthesis unit 16. If desired, an oxygenate or hydrocarbon stream can be co-fed to olefin synthesis unit 16 with the methanol, and a diluent if desired, as a stream 15. The olefin synthesis unit 16 converts methanol into olefins and separates the olefins into olefin product streams. Stream 18 is a propylene product stream. Stream 20 is an ethylene product stream. All or a portion of ethylene stream 20 is fed into ethylene oxide reaction unit 22. Ethylene oxide reaction unit 22 produces an ethylene oxide stream 24, and a carbon dioxide stream 26. The ethylene oxide stream 24 can then be sent for further processing. Carbon dioxide stream 26 is fed into methanol synthesis unit 12, completing the loop.

Having now fully described this invention, it will be appreciated by those skilled in the art that the invention can be performed within a wide range of parameters within what is claimed, without departing from the spirit and scope of the invention:

What is claimed is:

1. A method of making methanol, comprising:

introducing an ethylene stream into an ethylene oxide reaction unit;

forming an ethylene oxide product within the ethylene oxide reaction unit;

removing the ethylene oxide product and a carbon dioxide containing vent stream from the ethylene oxide reaction unit;

producing a syngas stream from the carbon dioxide vent stream; and producing methanol from the syngas stream.

2. A method as claimed in claim 1, wherein the syngas stream has a SN of from about 1.4 to about 2.4.

3. The method as claimed in claim 1, wherein the syngas stream is produced in a steam reformer.

4. The method as claimed in claim 1, wherein the syngas stream is produced in a partial oxidation reformer.

5. A method as claimed in claim 1, wherein the methanol is fed to an olefin synthesis reactor.

6. A method as claimed in claim 5, wherein the olefin synthesis reactor contains a molecular sieve catalyst.

7. method as claimed in claim 6, wherein the molecular sieve catalyst comprises a silicoaluminophosphate molecular sieve selected from SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, or mixtures thereof.

8. A method as claimed in claim 1, wherein the ethylene oxide reaction unit comprises a catalyst.

9. A method as claimed in claim 8, wherein the catalyst is a silver containing catalyst.

\* \* \* \* \*

UNITED STATES PATENT AND TRADEMARK OFFICE
CERTIFICATE OF CORRECTION

PATENT NO. : 6,495,609 B1  
DATED : December 17, 2002  
INVENTOR(S) : Ronald G. Searle It is certified that error appears in the above-identified patent and that said Letters Patent is hereby corrected as shown below:

<u>Column 3,</u>  
Line 57, remove the word "may".

Signed and Sealed this

Twenty-sixth Day of August, 2003

JAMES E. ROGAN  
*Director of the United States Patent and Trademark Office*